(12) United States Patent
Fernandez

(10) Patent No.: US 7,593,783 B2
(45) Date of Patent: Sep. 22, 2009

(54) RECONFIGURABLE GARMENT DEFINITION AND PRODUCTION METHOD

(76) Inventor: Dennis S. Fernandez, 1175 Osborn Ave., Atherton, CA (US) 94027

( * ) Notice: Subject to any disclaimer, the term of this patent is extended or adjusted under 35 U.S.C. 154(b) by 351 days.

(21) Appl. No.: 11/588,717

(22) Filed: Oct. 27, 2006

(65) Prior Publication Data

US 2007/0067885 A1 Mar. 29, 2007

(51) Int. Cl.
*G06F 19/00* (2006.01)
(52) U.S. Cl. .................................................... 700/132
(58) Field of Classification Search ......... 700/130–141; 340/286.01, 321, 574, 573.1; 2/15, 426
See application file for complete search history.

(56) References Cited

U.S. PATENT DOCUMENTS

| | | | | |
|---|---|---|---|---|
| 2,856,466 | A | * | 10/1958 | Gustafson et al. ............ 381/327 |
| D207,919 | S | * | 6/1967 | Fai .............................. D16/309 |
| D212,863 | S | * | 12/1968 | Roberts ....................... D14/192 |
| 3,769,663 | A | * | 11/1973 | Perl .............................. 24/3.3 |
| 4,283,127 | A | * | 8/1981 | Rosenwinkel et al. ........ 351/158 |
| 4,683,587 | A | * | 7/1987 | Silverman ................... 381/311 |
| 4,856,086 | A | * | 8/1989 | McCullough ............... 455/344 |
| 4,882,769 | A | * | 11/1989 | Gallimore .................... 455/344 |
| 5,020,150 | A | * | 5/1991 | Shannon ................... 455/343.1 |
| 5,404,385 | A | * | 4/1995 | Ben-Haim ................... 377/24.2 |
| 5,414,405 | A | | 5/1995 | Hogg et al. |
| 5,563,951 | A | * | 10/1996 | Wang et al. ................... 381/301 |
| 5,568,126 | A | | 10/1996 | Andersen et al. |
| 5,606,743 | A | * | 2/1997 | Vogt et al. .................... 455/347 |
| 5,715,323 | A | * | 2/1998 | Walker ......................... 381/385 |
| 5,745,034 | A | | 4/1998 | Andersen et al. |
| 5,757,661 | A | | 5/1998 | Surville |
| 5,768,135 | A | | 6/1998 | Part et al. |
| 5,850,222 | A | | 12/1998 | Cone |
| 6,010,216 | A | * | 1/2000 | Jesiek .......................... 351/158 |
| 6,023,241 | A | * | 2/2000 | Clapper ................... 342/357.13 |
| 6,046,712 | A | * | 4/2000 | Beller et al. .................... 345/8 |
| 6,091,546 | A | * | 7/2000 | Spitzer ......................... 359/618 |
| 6,091,832 | A | * | 7/2000 | Shurman et al. ............. 381/381 |
| 6,150,998 | A | * | 11/2000 | Travers et al. ................... 345/8 |
| 6,198,394 | B1 | | 3/2001 | Jacobsen et al. |
| 6,246,994 | B1 | | 6/2001 | Wolven et al. |
| 6,281,788 | B1 | | 8/2001 | Noll |
| 6,349,001 | B1 | * | 2/2002 | Spitzer ......................... 359/618 |
| 6,408,330 | B1 | | 6/2002 | DeLaHuerga |
| 6,409,338 | B1 | * | 6/2002 | Jewell .......................... 351/158 |
| 6,435,386 | B2 | | 8/2002 | Scott |
| 6,473,671 | B1 | | 10/2002 | Yan |
| 6,474,367 | B1 | | 11/2002 | Jayaraman et al. |
| 6,483,483 | B2 | | 11/2002 | Kosugi et al. |
| 6,516,240 | B2 | | 2/2003 | Ramsey et al. |
| 6,545,606 | B2 | | 4/2003 | Piri et al. |
| 6,564,118 | B1 | | 5/2003 | Swab |
| 6,725,124 | B2 | | 4/2004 | Yan |

(Continued)

OTHER PUBLICATIONS

U.S. Appl. No. 10/752,060, filed Jan. 5, 2004, Fernandez.

(Continued)

*Primary Examiner*—Danny Worrell
(74) *Attorney, Agent, or Firm*—Fernandez & Associates, LLP

(57) ABSTRACT

Computer-aided design and manufacture software and hardware automate garment and fashion definition and production. Configurable garment includes ornamental element, pattern display, and personal identifier and wireless sensor electronics.

16 Claims, 4 Drawing Sheets

U.S. PATENT DOCUMENTS

| | | | |
|---|---|---|---|
| 6,729,726 B2* | 5/2004 | Miller et al. | 351/158 |
| 6,769,767 B2* | 8/2004 | Swab et al. | 351/158 |
| 6,874,127 B2 | 3/2005 | Newell et al. | |
| 6,911,172 B2* | 6/2005 | Swab et al. | 264/250 |
| 6,929,365 B2* | 8/2005 | Swab et al. | 351/153 |
| 6,966,647 B2* | 11/2005 | Jannard et al. | 351/158 |
| 7,013,009 B2* | 3/2006 | Warren | 379/420.01 |
| 7,147,324 B2* | 12/2006 | Jannard et al. | 351/158 |
| 7,231,038 B2* | 6/2007 | Warren | 379/420.01 |
| 7,445,332 B2* | 11/2008 | Jannard et al. | 351/158 |
| 7,461,936 B2* | 12/2008 | Jannard | 351/158 |
| 2002/0004763 A1 | 1/2002 | Lam | |
| 2002/0021297 A1 | 2/2002 | Weaver | |
| 2002/0039170 A1* | 4/2002 | Jannard et al. | 351/142 |
| 2003/0011590 A1 | 1/2003 | Kung et al. | |
| 2003/0151118 A1 | 8/2003 | Baude et al. | |
| 2003/0152691 A1 | 8/2003 | Baude et al. | |
| 2003/0196239 A1 | 10/2003 | Zic et al. | |
| 2003/0208830 A1 | 11/2003 | Marmaropoulos et al. | |
| 2003/0212319 A1 | 11/2003 | Magill | |
| 2003/0214408 A1 | 11/2003 | Grajales et al. | |
| 2003/0215632 A1 | 11/2003 | Jen | |
| 2004/0029582 A1* | 2/2004 | Swab et al. | 455/426.1 |

OTHER PUBLICATIONS

U.S. Appl. No. 11/027,819, filed Dec. 29, 2004, Fernandez.
"Can a dress replace a doctor? Will we wear buildings? Will clothing replace computers? Can one garment replace 100?", 6 pgs.
Grant, Glenn, "Smart Fabrics," Freelance Traveller, 4 pgs.
Davis, Robert, "Smart T-shirts' know when something is wrong Applications abound, from babies at home to soldiers at war," USA Today.com, Nov. 17, 1998, 2 pgs.
"Power Dressing Could Spark A Trend," www.globaltechnoscan.com, 3 pgs.
Sondhi, Anjali, "Invention: Key to Survival," www.Imagesfashion.com, 2 pgs.
Johnson, R.Colin, "Nano research eyes ink jet-printed 'sheets' of circuits," EETimes, Nov. 20, 2003, 3 pgs.
Mokhoff, Nicolas, "OLED contracts go to military suppliers," EETimes, Nov. 11, 2003, 1 pg.
"Intelligent Clothing Introduction," www.intelligentclothing.com, 8 pgs.
"Space, textile and information technologies: a unique combination of expertise for the development of a new generation of communicating . . . ," Virtual Medical Worlds, 4 pgs.
"Smart biomedical clothes promising way to keep the European citizen healthy," Virtual Medical Worlds, 4 pgs.
Goettling, Gary, "Weaving Technology into Shirts," Building the Future, 2 pgs.
"Wearable Computers in the Medical Profession," Tomorrows Technology for Teachers, Dec. 1999, 2 pgs.
'Body Handles Nanofiber Better', Nanotechnology, Jan. 2004; http://www.technologyreview.com.
Wood, Lamont, "Weaving new functions into fashion," Chicago Tribune Online Edition, Oct. 28, 2002, 3 pgs.
"Where fabrics meet electronics, " SOFTswitch Media Release, 4 pgs.
Verma, S.S., "Wearable Electronic clothes," The Tribune Online Edition, Nov. 20, 2003, 3 pgs., Chandigarh, India.
Marculescu, et al., "Ready To Ware," IEEE Spectrum Online, Nov. 22, 2003, 5 pgs.
Post, et al., "Smart Fabric, or Washable Computing," 4 pgs.
"2003 IEDM Technical Program 2003," IEEE International Electron Devices Meeting, 2 pgs.
Krane, Jim, "Telltale Clothes," CBSNews.com, 2 pgs., New York.
Eisenberg, Anne "For the Smart Dresser, Electric Threads That Cosset You", The New York Times, Feb. 6, 2003, p. G. 7.
Ruibal, Sal. "Winter Coat Packs Its Own Thermostat", USA Today, Mar. 14, 2002, Sports, p. 16c.
"Sytleborg: Fashion Archieves" Styleborg, Wearable Technology, Textiles, Fashion and other semi-related topics. WWW. Styleborg.com.
Piquepaille, Roland. "Smart Clothing: A fashion show". http://radio.weblogs.com/.
Berzowska, Joey. "Second Skin and Software". Http://hybrid.concordia.ca/~joey/classes/skin/rescources.html.
Salkever, Alex. "The many Shapes of Tomorrow's PC". Businessweek Online, Nov. 4, 2003.
Starner, Thad, "Human Powered Wearable Computing". 328 Appears IBM Systems Journal, col. 35, No. 3 & 4.
Kerber, Ross, "Malden Mills' Next Hot Produc: Fabrics That Heat Up," Boston Globe, Oct. 22, 2001, 2 pgs., Boston, MA.
Sullivan, Andy "PluggedIn: Cutting-Edge Science Creates Stain-Free Pants". Reuters, Jul. 27, 2003.
Claiming Infringement, Patent Owner of Computer Systems for Personalized Fashion Shopping Andrea Rose Files Suit Against Public Technologies . . . , Oct. 19, 1999, 3 pgs.
Knapp, Louise, "E-D Eyes Turn to Fashion World," Wired News, Aug. 30, 2003, 3 pgs.
Eric Sylvers, "In Milan, Working to Unfurl a High-Tech Blanket of Fiber," The New York Times, Nov. 3, 2003, 3 pgs.
"Nanowires Boost Plastic Circuits," Technology Review, Oct. 20, 2003, 2 pgs.
Brown, Chappell, "E-textiles, robot 'skin' among advances at IEDM," EE Times, Oct. 9, 2003, 2 pgs.
"Rudolf Tromp to receive the Davisson-Germer Prize," IBM Research News, 4 pgs.
"The Pentacene Project," IBM Research, 4 pgs.
"Heart Patients May benenfit from Sensors in Clothes," Reuters, Oct. 8, 2003, 1 pg.
Product Concepts, Universal Display Corporation, 3 pgs.
Intellectual Property, Universal Display Corporation, 2 pgs.
Cambridge Display Technology Fact Sheet, 6 pgs.
Lindwer, et al. "Ambient Intelligence Visions and Achievements: Linking Abstract Ideas to Real-World Concepts," IEEE, 2003, 6 pgs.
Donev, Eugene, "Design and Implementing Organic Thin-Film Transistors (OTFTs)," Sep. 2002, 9 pgs., University of the South, Sewanee, Tennessee.
"Nanomaterials, Soft Matter, and Electronic Materials Find Common Ground at 2003 MRS Spring Meeting," MRS Bulletin, Jul. 2003, pp. 517-534.
"Wearable Computing," Recent Papers.
DeVaul, et al., "MIThril: context-aware computing for daily life," Massachusetts Institute of Technology, May 16, 2001, 9 pgs.
Keyes, Edward, "The Enchantment Window Manager: A Wearable Computing User Interface," Aug. 24, 2000, 13 pgs.
De Vaul, et al., "The Ektara Architecture: The Right Framework for Context-Aware Wearable and Ubiquitous Computing Applications," Massachusetts Institute of Technology, 7 pgs.
Starner, et al., "Visual Contextual Awareness in Wearable Computing Perceptual Computing TR#465 MIT Laboratory," Massachusetts Institute of Technology.
Sawhney, et al., "Nomadic Radio: Scalable and Contextual Notification for Wearable Audio Messaging," Proceedings of CHI'99, 1999, 8 pgs., Pittsburgh Pennsylvania.
Clarkson, et al., "Auditory Context Awareness via Wearable Computing," MIT Media Laboratory, 6 pgs., Cambridge, MA.
Sawhney, et al. "Speaking and Listening on the Run: Design for Wearable Audio Computing," Proceedings of ISWC '98, Oct. 19-20, 1998, pp. 1-8.
Healey, et al., "StartleCam: A Cybernetic Wearable Camera," Proceedings of the Second International Symposium on Wearable Computers, Oct. 1998, pp. 1-8.
Colella, et al., "Participatory Simulations: Using Computational Objects to Learn about Dynamic Systems," CHI' 98 Participatory Simulations, 1998, 3 pgs.
Schiele, Bernt, "DyPERS: A Dynamic Personal Enhanced Reality System," Jul. 13, 1998, 6 pgs.
Rhodes, Bradley J., "The wearable remembrance agent: a system for augmented memory," Personal Technologies Journal Special Issue on Wearable Computing, 1997, 10 pgs.

Rhodes, Bradley J., "The wearable remembrance Agent A system for augmented memory," The Proceedings of the 1st International Sysmposium on Wearable Computing, Oct. 1997, 8 pgs.

Jebara, et al., "Stochasticks: Augmenting the Billiards Experience with probabilistic Vision and Wearable Computers," Massachusetts Institute of Technology, Feb. 18, 1998.

Starner, et al., "Real-Time American Sign Language Recognition Using Desk and Wearable Computer Based Video," Massachusetts Institute of Technology.

Sparacino, et al., "Wearable Cinema/Wearable City: bridging physical and virtual spaces through wearable computing," MIT Media Lab, pp. 1-10.

Rhodes, et al., "Wearable Computing Meets Ubiquitous Computing," The Proceedings for the Third International Symposium on Wearable Computers, Oct. 18-19, 1999, 12 pgs.

Sparacino, et al., "Technologies and methods for interactive exhibit design: from wireless object and body tracking to wearable computers," MIT Media Lab, pp. 1-9.

Healey, et al., "Quantifying Driver Stress: Developing a System for Collecting and Processing Bio-Metric Signals in Natural Situations," MIT Media Laboratory, pp. 1-6.

Healey, et al., "A New Affect-Perceiving Interface and Its Application to Personalized Music Selection," Proceedings of the 1998 Workshop on Perceptual User Interfaces, 1998.

Starner, et al., "A Wearable Computer Based American Sign Language Recognizer," Massachusetts Institute of Technology, 8 pgs.

Tan, et al., "Tactual Displays for Wearable Computing," Personal Technologies, 1997, pp. 225-230, Cambridge, MA.

Picard, et al., "Affective Wearables," Personal Technologies, 1997, pp. 1-11, vol. 1.

Healey, et al., "Digital Processing of Affective Signals," Proceedings of the ICASSP '98, 1998, pp. 1-5.

Roy, et al, "Wearable Audio Computing: A Survey of Interaction Techniques," MIT Media Laboratory, 12 pgs.

Mann, Steve, "Wearable Computing: A First Step Toward Personal Imaging," www.Computer.org, 1997, 2 pgs.

Starner, et al. "Augmented Reality Through Wearable Computing," Presence, Special Issue on Augmented Reality, 1997.

Rhodes, et al., "Remembrance Agent, A continuously running automated information retrieval system," 7 pgs.

Mann, Steve, "Mediated reality," MIT-ML Percom TR-260, 1994, pp. 1-21.

Picard, R.W., "Affective Computing," M.I.T. Media Laboratory Perceptual Computing Section Technical Report No. 321, pp. 1-26.

Starner, Thad, "The Cyborgs are Coming or The Real Personal Computers," 1994, 10 pgs.

Sawhney, et al., "Design of Spatialized Audio in Nomadic Environments," International Conference on Auditory Display, 1997, 8 pgs.

Steven J. Schwartz, et al. "The Smart Vest: Towards a Next Generation Wearable Computing Platform," Jul. 1999, 7 pages.

* cited by examiner

Ornament
101

Power Source
104

Identifier/Sensor
102

Pattern Display
103

Networking
Interface
105

Figure 1

RECONFIGURABLE GARMENT DEFINITION AND PRODUCTION METHOD

CROSS-REFERENCE TO RELATED APPLICATION

This application is based on U.S. patent application Ser. No. 11/027,819 filed originally on Dec. 29, 2004, which is a continuation patent application corresponding to parent patent application Ser. No. 10/752,060 filed originally on Jan. 5, 2004, issued as patent 6,882,897 on Apr. 19, 2005.

FIELD OF INVENTION

Invention relates to computer-assisted methods for novel garment design and manufacture, particularly software, databases and related electronic networks and sensors.

BACKGROUND OF INVENTION

Conventional fashion industry employs various creative manual processes to design and produce new clothes. However, conventional techniques are limited to the extent that garment design and production processes are not easily customized, time constrained, and are not reconfigurable easily. For example, customer has to wait at cashier, try various kinds of clothes in a changing room, take a lot of measurements, inaccurately customize the garment, or buy standardized garment to speed up the purchasing process.

Accordingly, there is a need for improved definition and production efficiency by using some electronic automation techniques, for example, to assist prototype design, garment customization, and garment grading. Furthermore, to increase customer satisfaction guarantee of manufactured garment, various computer-aided methods for customer to input their body profile information and view their appearance with designed garment are used.

Various fabric or garment with integrated flexible information infrastructure and electrode/sensors, various methods of representing customer body profile information in different formats, and various methods for assisting a customer to select properly sized apparel have been discussed in the prior art may be used to enable this invention.

This application describes an electronic process for assisting customer to directly design a customized garment with the help of either human or computer fashion advisor. Thus, the invention resembles a virtual store with a fashion advisor. User can confidently design and purchase the garment at anytime.

SUMMARY

Computer-aided design and manufacture software and hardware automate garment and fashion definition and production. Configurable garment and fashion includes ornamental element, pattern display, and personal identifier and wireless sensor electronics, integrating the business world of fashion and consumer electronics.

A computer supported process especially configured for user to easily design reconfigurable apparel, input body profile information, input assembly and test preferences, receive and give recommendation whether the garment fit the body profile to assist user in making a purchasing decision. All information resulting from the process can be protected and are accessible only for pre-determined user.

BRIEF DESCRIPTION OF FIGURES

The accompanying drawings which are incorporated in and form a part of this specification, illustrate embodiments of the invention and together with the description, serve to explain the principles of the invention:

FIG. 1 is a diagram showing a representative configurable garment according to an embodiment of the present invention.

DETAILED DESCRIPTION

Figure 2:
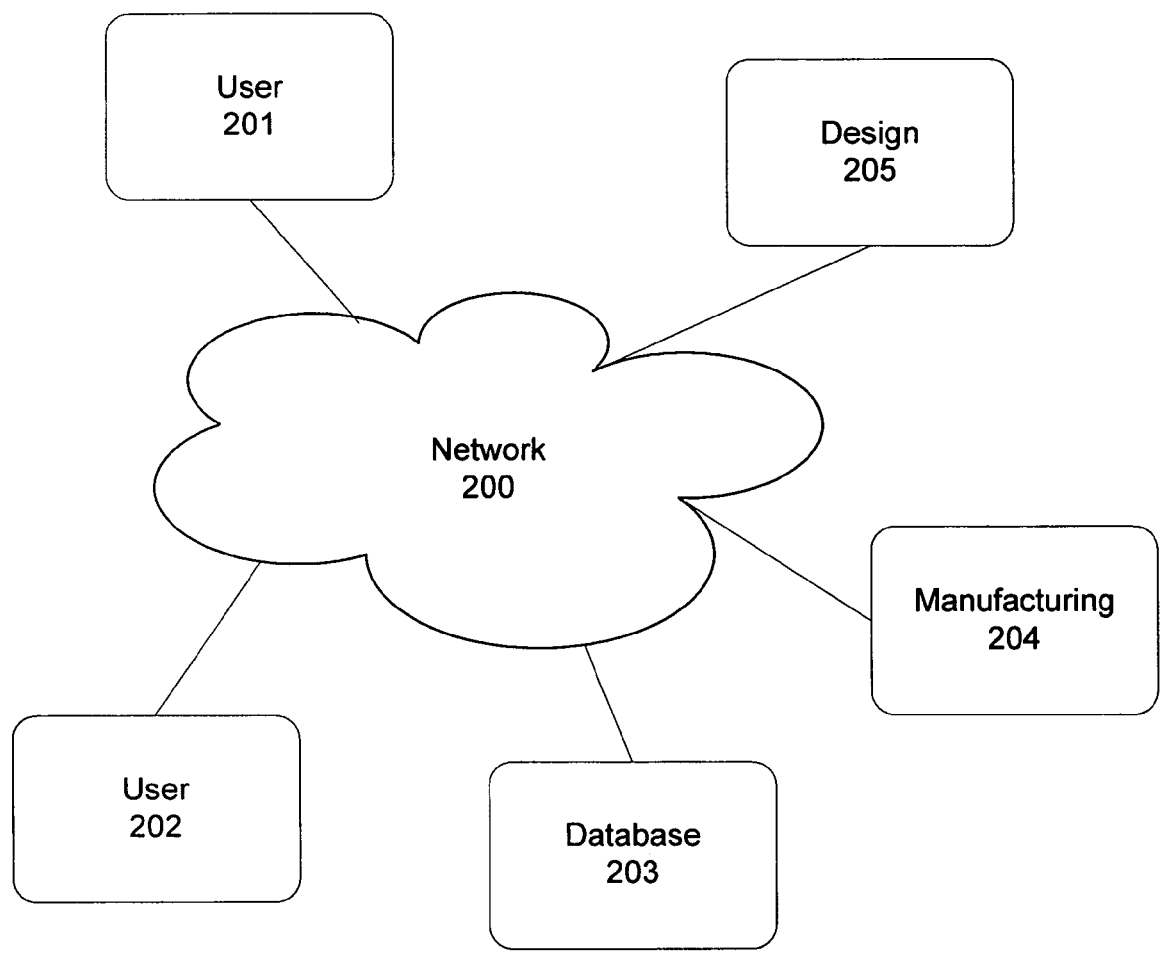
FIG. 2 is a generalized diagram of network system according to an embodiment of the present invention.

Reference is made in detail to the preferred embodiments of the invention. While the invention is described in conjunction with the preferred embodiments, the invention is not intended to be limited by these preferred embodiments. On the contrary, the invention is intended to cover alternatives, modifications and equivalents, which may be included within the spirit and scope of the invention as defined by the appended claims. Furthermore, in the following detailed description of the invention, numerous specific details are set forth in order to provide a thorough understanding of the invention. However, the invention may be practiced without these specific details. In other instances, well-known methods, procedures, components, and circuits have not been described in detail so that aspects of the invention will not be obscured.

FIG. 1 is a diagram showing representative configurable garment 100 according to an embodiment of the present invention. As understood herein, the term garment is interpreted and construed broadly to mean any wearable items and/or their accessories, such as shirts, pants, jeans, slacks, shorts, skirts, khakis, glasses, shoes, scarf, jacket, ties, belts, socks and wallet.

Garment 100 comprises programmable electronic devices, such as ornament 101, identifier and/or sensor 102, pattern display 103, power source 104 and networking interface 105.

Ornament 101 comprises electronic devices incorporated into garment 100, including music player, global positioning system, antenna, mobile phone, computer, television, alarm, camera, switch and electroluminescent lamp. The ornaments are washable and detachable using well-known techniques in the art. Ornament 101 also enables garment to function as interface to control any type of electronic device. For example, a jacket that interfaces with light switches or a television remote control. Ornament 101 has an optional property to disregard chemical rays that can possibly cause cancer, disregard sources of bio/chemical terrorism or nuclear threats. Ornament 101 enables garment and fashion 100 to be stain free, therefore not requiring the use of detergent and materially enhance environmental quality. Ornament 101 assures that clothes do not contain disease, and are safe from HIV/AIDS and other diseases. Optionally, ornament 101 plays music based on user emotion detected by human emotion detector integrated in the garment.

Sensor 102 comprises identifier or sensors integrated with garment 100. Sensor 102 comprises medical sensors, temperature/heat sensors, optical sensors, accelerometer, electromagnetic sensors, human emotion detector, pollution rate detector, water sensors, motion sensor, and microphones. Medical sensors measure physical information such as heart rate, blood pressure, and other vital signs and also detect and diagnose diseases such as HIV/AIDS, cancer, etc. Sensor 102 detects bombs/military equipments particularly for safety inspection purpose. Sensor 102 can be integrated into the garment through multiple ways well known in the art.

In future advancement, sensor 102 and ornament 101 may resemble ambient intelligence in that it is invisible, present whenever user needs it, enabled by simple and effortless interaction and autonomously acting adaptively to user and context.

Pattern display 103 as a graphical communication interface is a flexible optical fiber screen or optical fibers woven into clothes capable of downloading and displaying graphics such as logos, texts, patterns, and images directly onto clothes. Based on electrical commands, pattern display 103 may change color, images, projections, and patterns using electrical power provided by power source 104. Pattern display 103 also offers access to services such as internet, video, and e-commerce as well as displays sensor 102, power source 104 and ornament 101 data. For example, sporting clothes monitor hear rate and blood pressure during a gym workout and displays them on its pattern display 103, or pattern display 103 of clothing fitted with global positioning system worn by skiers or mountaineers displays its geographic location.

Sensor 102 and pattern display 103 may be distributed in a regular grid.

Power source 104 provides power for garment 100, and comprises AC/DC source, portable rechargeable battery, fuel cell, environment heat source, mechanical source, light source, and/or other source for providing electrical power. Specifically, environmental heat source is produced by tapping the natural heat given off by the body, mechanical heat source is produced by transforming mechanical energy of user movement into electrical power, and optical heat source is produced by transforming surrounding light into electrical power. The use of environmental heat source, mechanical heat source and optical heat source as power source 104 reduces regular battery usage, and therefore materially enhance the quality of the environment.

Garment 100 optionally employs heat sink to reduce heat trapped inside clothes, so that garment 100 has more efficient utilization and conservation of energy resources provided by power source 104.

Networking interface 105 communicates via radio wave, wired or wireless network to provide garment 100 internal and external communications with user and database. Flexible conductive fibers are woven into the garment to transmit signals inside the garment. The conductive fibers may be interwoven with the material of a garment, or added to it in narrow strips of ribbon that are sewn at certain places. Optionally, garment may be made from electrotextile, where yarns made of synthetic or metallic fibers are knitted into cotton or polyester. The yarn bundle is clad with metal, silver or nickel, and then insulated with a polymer. The conductive fibers are connected to power source 104 to create circuits.

Networking interface 105 allows user to control ornament 101, sensor 102, pattern display 103, and power source 104 through user data input devices such as touchpad, voice recognition tool, keypad, and so forth. Networking interface 105 connects garment 100 with user interface appliance 300, assembly source 407 and database 403. For example, networking interface 105 sends identifier/sensor 102 data, power source 104 status data, or pattern display 103 information to a database, and receives electrical commands from assembly source 407.

Garment 100 conforms to a governmental regulatory as proved by a testing process.

In one example, the garment is attached to a set of motorized frames that people with disabilities can wear to help them walk, climb steps, and so forth. The battery-powered plastic frame attached to the garment relies on electrodes attached to the garment detecting from the skin motor nerve signals emitted by the brain just before they instruct muscle cells to contract, thereby providing a real-time instruction for the frame to move in synchronize with the user.

In another example, sensor 102 embedded in the garment provides military, security and surveillance functions. Optical fibers and special sensors inside the garment detect bullet wounds and monitors body vital signs during combat conditions. Sensor 102 embedded in carpets, wallpapers and various kinds of canvas covers detects unrecognized person.

In another example, doctors design and purchase customized garment for each of their patients. Sensor 102 printed on the fabric allows doctor to monitor patients without having to keep them in hospital. The networking interface 105 transmits sensor 102 data to a doctor's computer or PDA, or sounds the alarm if sensor 102 senses a problem. Further sensor 102 applications enable garment worn to medicate or diagnose a disease.

Cutting electronic cloth makes it difficult to make good connections between different parts of the same garment and could be solved by manufacturing seamless clothing, to avoid the cutting and stitching problem altogether.

Security and privacy of garment 100 is well maintained.

FIG. 2 is a diagram showing sample digital electronic network interconnecting various accessible devices, hosts, computers, servers, or other processor and/or storage, such as user 201, memory or storage 203, design processor 204, and manufacturing processor 205. User 201 may access or store information stored in storage 203 through the network. Design source 204 runs the design process as controlled by user 201 and manufacturing source 205 runs the manufacturing and testing process. There are no limitations on their geographic location.

Figure 3:
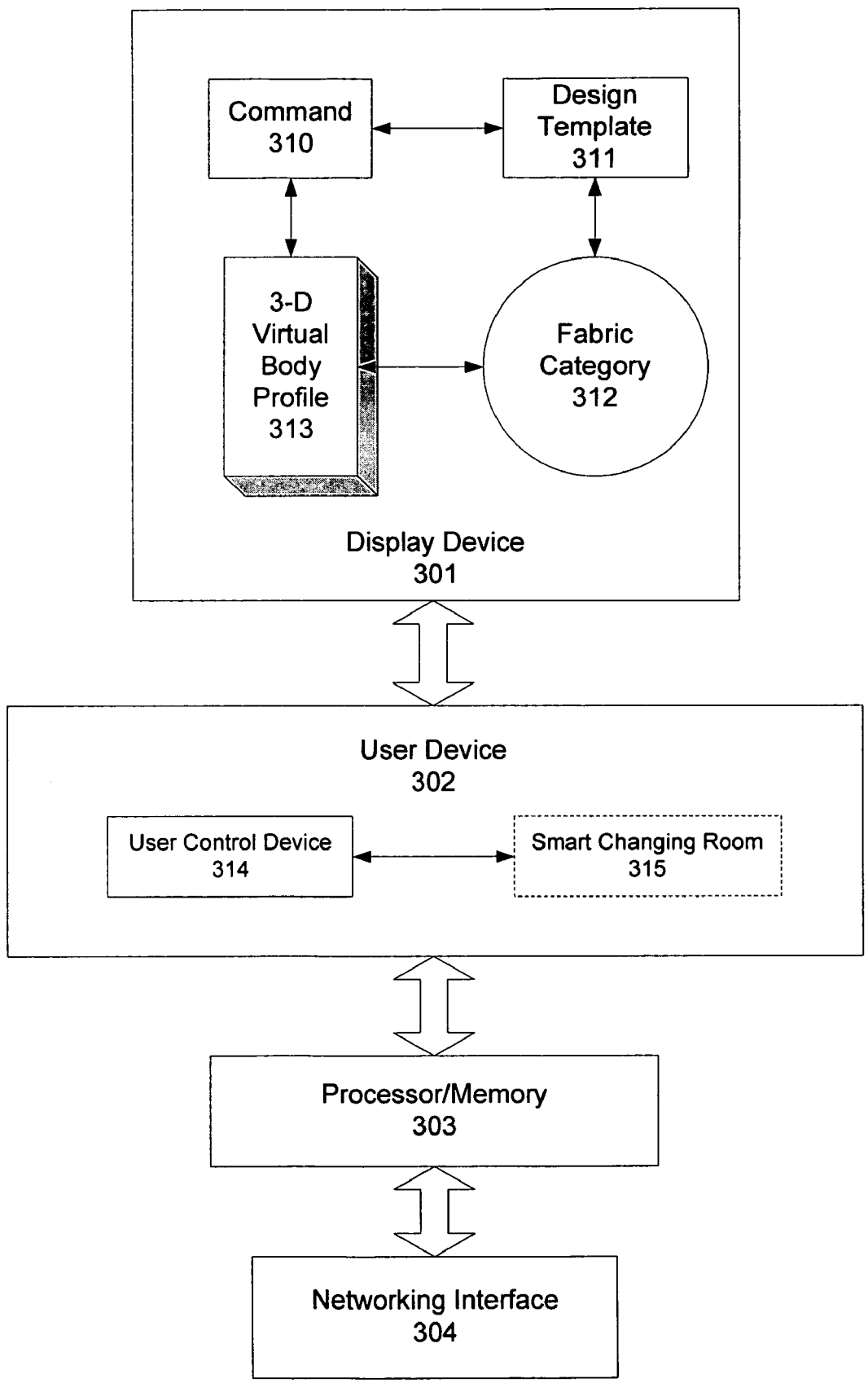
FIG. 3 is a diagram showing a user-interface appliance according to an embodiment of the present invention.

FIG. 3 is a diagram showing user interface appliance 300 according to an embodiment of the present invention. Appliance 300 comprises display device 301, user device 302, memory/processor 303, and networking interface 304.

User interface appliance 300 employs Graphical User Interface (GUI) in its program. As understood herein, the term GUI is interpreted and construed broadly to mean any graphical display system for representing the input and output of a program that displays certain icons, buttons, dialogue boxes, in its windows on the screen. User interface appliance 300 has a program known as user interface appliance 300 program that allows GUI to receive information from users, display garment design, display 3-D user body profile with or without wearing garment 100, process and store information, and communicate with network. User interface appliance 300 can be accessed anywhere, at a store or through internet.

Display device 301 here interpreted as an electronics display device contains an image-displaying region providing a visual representation of user interface appliance 300 program and user's interactions with user interface appliance 300 program. Display device 301 comprises command 310, design template 311, fabric category 312, and 3-D virtual body profile 313.

Command 310 comprises icons, buttons and dialogue boxes that represent user's communication with user interface appliance 300. Command 310 is coupled with user tool 302 to display user interaction with user interface appliance 300 program. Through command 310, user chooses a variety of options when configuring the garment definition. As understood herein, the term garment definition is interpreted to mean any garment property including design style, fabric category, and functional property.

It is noted that user is reminded that some options cannot be combined in the same garment. The options include, but not limited to, motion capture, phosphorescent, thermo-electric, electro-adhesive, variable color, variable shade, water shedding, bio monitors, electroluminescent, sound emitting/capturing, variable opacity, video display, force feedback, optical chameleon, photoelectric, computational array, self-repairing, touch sensitive, toxin filtering, voice recognition software, wireless communication device, variable rigidity, variable shape, variable reflectivity, thermal chameleon, self-cleaning.

User is also allowed to choose pre-configured templates such as work/leisure outfit, dance club gear, immersive media suit, covert ops bodysuit, adventure climber, exploration suit, backpack, utility vest, ultra tarpaulin, each of them contains pre-configured options.

User can check available garment material and sizes by interacting with command 310. User is also guided to design an architectural garment by providing or selecting functional property of garment 100, for example choosing a garment that could transform into tent, raincoat, massage chair, furniture, mattress, and medical wheelchair.

Design template 311 shows available choices of design template and/or user's current selection of design template. As understood herein, the term design template/style 311 is interpreted and construed broadly to mean any fashion design elements such as shirts style and sizes, collar design, pocket style and sizes, neck style, back details, sleeve details (length), cuffs, monograms, shirt fit, shirt size, shirt tail, stitching, and tie space.

Fabric category 312 shows choices of fabric category available and/or user's current selection of fabric category. As understood herein, the term fabric category 312 is interpreted and construed broadly to mean any material category such as patterns, material, color, stripes, solids, checks, texture, etc.

Once user control device receives a specific command from user, user interface appliance 300 program combines command 310, design template 311, and fabric category 312 information into a garment definition. User can add further information to the garment definition and generate a garment test script with the aid of verification source 404. For example, garment will only be purchased below a certain price range or the testing process should be focused on bio-medical sensor functionality.

3-D virtual body profile 313 is an image-processing device capable of displaying 3-D replica based on body profile information. Receiving a command from user, 3-D virtual body profile 313 displays a 3-D representation of body profile information with or without being superimposed by designed garment 100. 3-D virtual body shop 313 is coupled with verification source 407, thereby enabling 3-D virtual body shop 313 to also display the replica wearing the recommended garment.

User device 302 comprises user control device 314 and smart changing room 315. User control device 314 comprises mouse, joystick, keyboard, touchpad, and speech recognition software allowing user to control user interface appliance 300 program. For example, user moves a pointer on the screen (controlled by a mouse), selects certain objects by pressing buttons on the mouse while the pointer is pointing at them, touches and presses objects on display screen 301 to control the program, inserts text using keyboard and verifies information using speech recognition tool.

User control device 314 allows user to key in codes and fetch their own personalized garment definition to be displayed onto the display device 301. User control device 314 can be used to modify the 3-D body representation, such as modifying the height and adjusting the relative color contrast of the image and modify the garment property displayed on display device 301. User who has a body profile stored in a computer readable storage devices like flash memory, card, tag or disks should let user control device 314 to read the information and send it to 3-D virtual body profile 313.

Optionally, user tool 302 comprises a device to obtain a person body profile information, smart changing room 315. Smart changing room 315 comprises movable cameras distributed at key points around a room for extrapolating a three-dimensional replica of user. Various body profile parameters of the body profile information are to be measured according to the image captured. The resulting data is then saved by processor/memory 303 and fed into user interface appliance 300 program, which then transfer it to 3-D virtual body profile 313. 3-D virtual body profile 313 then uses this data to display a 3-D replica of a person with or without wearing designed garment and fashion 100.

Multiple angle snap shots are required to enable the system to more accurately measure or calculate many important parameters of the user body profile, such as the chest size, the waist size and the hips size. If the movable cameras capture continuous pictures, the playback of body profile can be used to combine with animated garment images to provide any motion effect. In many situations however, system may require manual assistance to obtain the most accurate result. Alternately, the body profile information can be made by referring to captured digital image such as photograph or video.

In order to increase the quality of recommendation received, user is encouraged to input more physical information, such as eye colors, eye shape, hair shape and color, skin color, face shape, height, body shape, shoulder line, etc. Users can also input their sizes (collar, waist, hip, yoke, inseam, thigh, skirts length, shorts length, knee length, ankle length, cuff lengths, etc.), and also their height and/or face structure. User may choose to use manual or electronic method to enter the information. In this embodiment, more than one user may access a same garment definition. If it is copyright protected, then user need to wait for permission to proceed with the next steps.

Processor/Memory 303 comprises information module for storage and/or retrieval of information about a user (such as account information, previous design templates, etc.), allowing user interface appliance 300 to be used by one or more users. Processor/Memory 303 may receive the information from a remote database or storage devices storing a library of garment definition. For example, database 403 provides a detailed information of a saved template required by user, database 403 provides a stored body template as requested by user, user's requiring a specific billing plan may require database to provide detailed explanation of the plan and his/her financial information, user's requiring a specific regulatory check may require database to provide such regulatory information, user's requiring that assembly and testing process take place at certain location require database to provide detailed location information to user.

As one advantage of this invention, user can easily reconfigure garment 100 design before or after receiving recommendation from verification source 407. Recommendation from verification source can be displayed by 3-D virtual body shop 313, spoken by speech tool of user control tool 314, or simply displayed by display screen 301.

Figure 4:
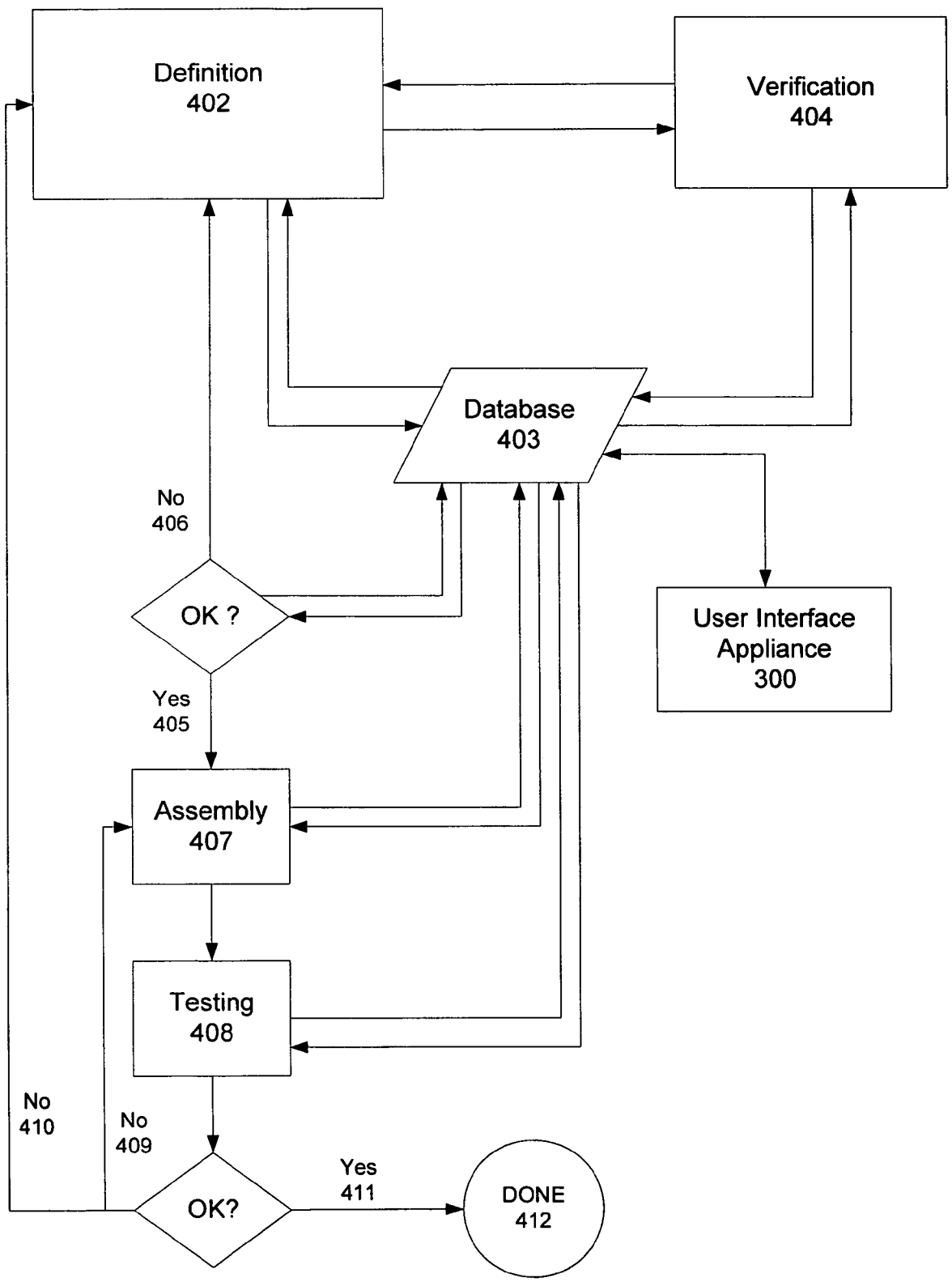
FIG. 4 is a flow diagram illustrating novel garment and fashion design and manufacturing process according to an embodiment of the present invention.

FIG. 4 is a flow diagram illustrating a garment design and manufacturing method according to an embodiment of the present invention. In the definition process user interface appliance 300 sends garment definition to database 403, which will transfer the information to definition source 402. Garment definition includes garment property and other information specified by user such as price range, governmental regulation and occupation. User can reset or stop the process at any time.

Referring now to verification process, definition source 402 sends the garment definition along with other information to verification source 404. Verification process may be done by one or more fashion and regulatory experts or by a computerized garment grading system. Verification source 404 checks regulatory requirements including environmental policy. Verification source 404 also optimizes the cost of the product by selecting appropriate garment material or assembly location. Verification source 404 checks whether the cost of designed garment 100 meets user's requirement. Verification source 404 is reconfigurable computer software that gives recommendation based on certain fashion trends that can be determined by user input. Verification source 404 as a computerized fashion consultant programmed to comment on user's apparel selection also acts as fashion advisor and gives fashion style recommendation. Verification source 404 also checks whether the garment definition meets functionality requirement determined by user.

Verification source 404 then sends all resulting information to database 403, which then sends them to user interface appliance 300 for user's confirmation. If user requires no additional process 405, all information is then sent to assembly source 407, else 406 proceed back with definition process 402 until done.

Assembly source 407 proceeds with manufacturing process. After manufacturing process is done, all manufacturing information is sent to database 403. Testing source 408 then receives the piece of garment 100 from assembly source 407 and a garment test script from database 403. Testing source 408 runs the test process and sends test result to database 403, which transfers the information to user through user interface appliance 300. If user requires no additional process 411, garment will be sent to user 412; else 409 go back to assembly process 407 or 410 go back to definition process 402.

The foregoing descriptions of specific embodiments of the invention have been presented for purposes of illustration and description. They are not intended to be exhaustive or to limit the invention to the precise forms disclosed. Modifications and variations are possible in light of the above teaching. Various novel embodiments to present endorsement scheme include, for example: digital network security or energy checking in residential, business, educational, or other working system context wherein one or more network-connected participants may endorse electronically in response to certain security-checking proposal according to present novel scheme; entertainment, theatrical, sports, or other broadband or media system context wherein one or more network-connected performer, staff or audience member may endorse electronically in response to certain live interactive proposal according to present novel scheme; and medical or healthcare system context wherein one or more network-connected patient, doctor, nurse or other staff may endorse electronically in response to certain medical diagnosis, interview, or other healthcare dialog according to present novel scheme.

The embodiments were chosen and described in order to explain the principles and the application of the invention, thereby enabling others skilled in the art to utilize the invention in its various embodiments and modifications according to the particular purpose contemplated. The scope of the invention is intended to be defined by the claims appended hereto and their equivalents.

I claim:

1. Electronically-configurable glasses comprising:
   wearable glasses;
   a media player coupled to the glasses; and
   an interface for electronically providing media to the media player,
   wherein software enables real-time user-control to configure media player operation, said software configuring electronically a variable color element, a variable shade element, a variable opacity element, a variable rigidity element, a variable shape element, or a variable reflectivity element according to a computerized expert or consultant program that stylistically recommends such element configuration of the glasses using a user template, parameter or sensed condition.

2. Glasses of claim 1 wherein:
   the interface provides wireless communication for downloading media from a network.

3. Glasses of claim 1 wherein:
   the media player comprises a mobile phone having an organic light emitting display and a portable fuel cell.

4. Glasses of claim 1 further comprising:
   a perfume or pheromone dispenser controllable by the software.

5. Glasses of claim 1 further comprising:
   a sensor coupled to the interface for sensing a patient condition or indicating a medical alarm.

6. Glasses of claim 1 wherein:
   the media comprises down-loadable music, such that usage thereof is chargeable financially to the user.

7. Glasses of claim 1 wherein:
   the software comprises a GUI for assisting user definition, configuration or selection according to a garment definition, design template or style, or expert design template.

8. Integrated glasses and music player apparatus comprising:
   glasses; and
   a music player coupled to the glasses,
   wherein the music player electronically or wirelessly accesses music media from a network, and software configures electronically a variable color element, a variable shade element, a variable opacity element, a variable rigidity element, a variable shape element, or a variable reflectivity element according to a computerized expert or consultant program that stylistically recommends such element configuration of the glasses using a user template, parameter or sensed condition.

9. Apparatus of claim 8 further comprising:
   a mobile phone having a global positioning locator.

10. Apparatus of claim 8 further comprising:
    a medical sensor coupled to the glasses for enabling a doctor or hospital computer to monitor a patient wearing the glasses; and
    an electronically-controlled medicine dispenser coupled to the glasses.

11. Apparatus of claim 8 further comprising:
    a human-emotion detector coupled to the glasses; and an electronically-controlled perfume or pheromone dispenser coupled to the glasses.

12. Apparatus of claim 8 wherein:
the music media is accessible using software for choosing, selecting, configuring or defining a garment definition, a design template or style, or an expert design template.

13. Method for configuring electronic glasses having media player comprising steps:
configuring a media player coupled to glasses for playing one or more media selection; and
accessing such selection wirelessly from a network;
wherein the configuring step electronically configures a variable color element, a variable shade element, a variable opacity element, a variable rigidity element, a variable shape element, or a variable reflectivity element according to a computerized expert or consultant program that stylistically recommends such element configuration of the glasses using a user template, parameter or sensed condition.

14. Method of claim 13 wherein:
the media player is configurable using GUI software for assisting user selection according to a garment definition, design template or style, or expert design template.

15. Method of claim 13 wherein:
the media player comprises a mobile telephone including an RFID device.

16. Method of claim 13 wherein:
the configuring step comprises simulating a prototype model or media application.

* * * * *